United States Patent [19]

Buettner

[11] Patent Number: 5,834,318
[45] Date of Patent: Nov. 10, 1998

[54] SCREENING OF COMBINATORIAL PEPTIDE LIBRARIES FOR SELECTION OF PEPTIDE LIGAND USEFUL IN AFFINITY PURIFICATION OF TARGET PROTEINS

[75] Inventor: Joseph A. Buettner, Raleigh, N.C.

[73] Assignee: Bayer Corporation, Berkeley, Calif.

[21] Appl. No.: 438,331

[22] Filed: May 10, 1995

[51] Int. Cl.$^6$ ........................................ G01N 33/53
[52] U.S. Cl. .......................... 436/518; 435/6; 435/7.1; 435/7.9; 435/7.92; 435/962; 435/967; 436/501; 436/524; 436/527; 436/528; 436/531; 436/532; 436/533; 436/534; 436/161; 436/802; 436/808; 436/815
[58] Field of Search .......................... 435/6, 7.1, 7.9, 435/5, 7.92, 962, 967; 436/501, 518, 524, 527, 528, 531, 532, 533, 534, 161, 807, 808, 815

[56] References Cited

U.S. PATENT DOCUMENTS 5,133,866  7/1992  Kauvar ..................................... 210/635

FOREIGN PATENT DOCUMENTS 9200091  1/1992  WIPO .

OTHER PUBLICATIONS

Furka, A., et al., "General method for rapid synthesis of multicomponent peptide mixtures," Int. J. Peptide Protein Res. 37: 487–493 (1991).

Lam, K.S., et al., "A new type of synthetic peptide library for identifying ligand binding activity," Nature 354: 82–84 (1991).

Meldal, M., et al., "Portion–mixing peptide libraries of quenched fluorogenic substates for complete subsite mapping of endoprotease specificity," Proc. Nat. Acad. Sci. USA 91: 3314–3318 (Apr. 1994).

Vagner, J., et al., "Novel methodology for differentiation of 'surface' and 'interior' areas of polyoxyethylene–polystyrene (POE–PS) supports: application to library screening procedures," in Innovative Perspectives in Solid Phase Synthesis (R. Epton, ed., 1994), pp. 347–352.

Lam, K.S., et al. "Application of a dual color selection scheme in the screening of a random combinatorial peptide library," J. Immunol. Meth. 180: 219–223 (1995).

Lebl, M., et al., "One–bead–one–structure combinatorial libraries," Biopolymers (Peptide Science) 37: 177–198 (1995).

*Primary Examiner*—Lora M. Green
*Attorney, Agent, or Firm*—James A. Giblin; Michael A. Beck

[57] ABSTRACT

Ligands that interact with a target can be more easily identified if false positive interactions (either specific or non-specific) from the detecting system are differentiated from the target-specific interaction. An improved method of identifying peptides which bind with a target protein is presented. The steps are: binding a random library of peptides to a support material, allowing detection reagents to contact the peptides and the support material then identifying these interactions, then allowing the target protein to selectively bind to the peptides, allowing detection reagents to contact the bound target protein, and characterizing the peptide bound to the identified support material. Interaction of a ligand or the support material with the detection reagents will cause a distinct color change which distinguishes those ligands which selectively bind to target protein. The characterized peptide can then be used in affinity purification of the target protein. In one embodiment, automation of the assay is demonstrated by flowing all immunoreagents through the beads in a column format ensuring highly efficient washing. In the preferred embodiment, a resin for peptide synthesis which is hydrophilic, contains spacers and may exhibit less nonspecific background than other resins permits synthesis and direct evaluation of combinatorial peptide libraries for binding to target proteins is utilized. Examples for the use of this new resin and methodology for identifying peptide-ligands for purification of proteins are presented.

19 Claims, 9 Drawing Sheets

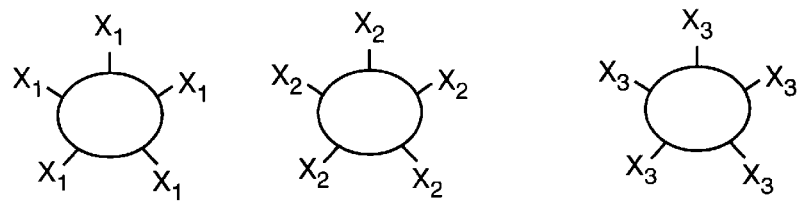
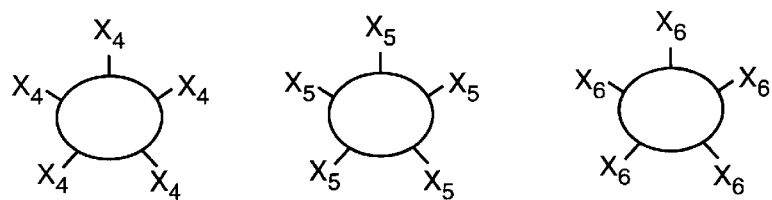
FIG._1A
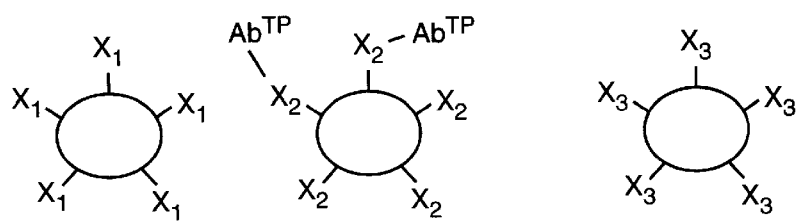
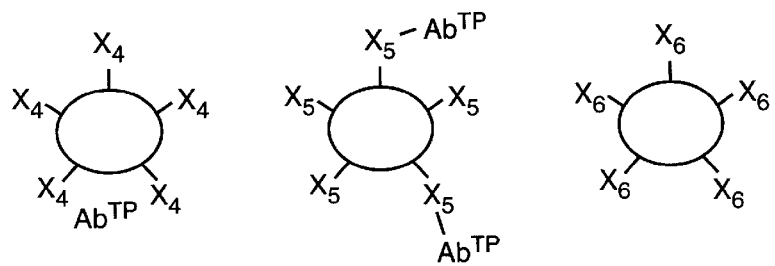
FIG._1B

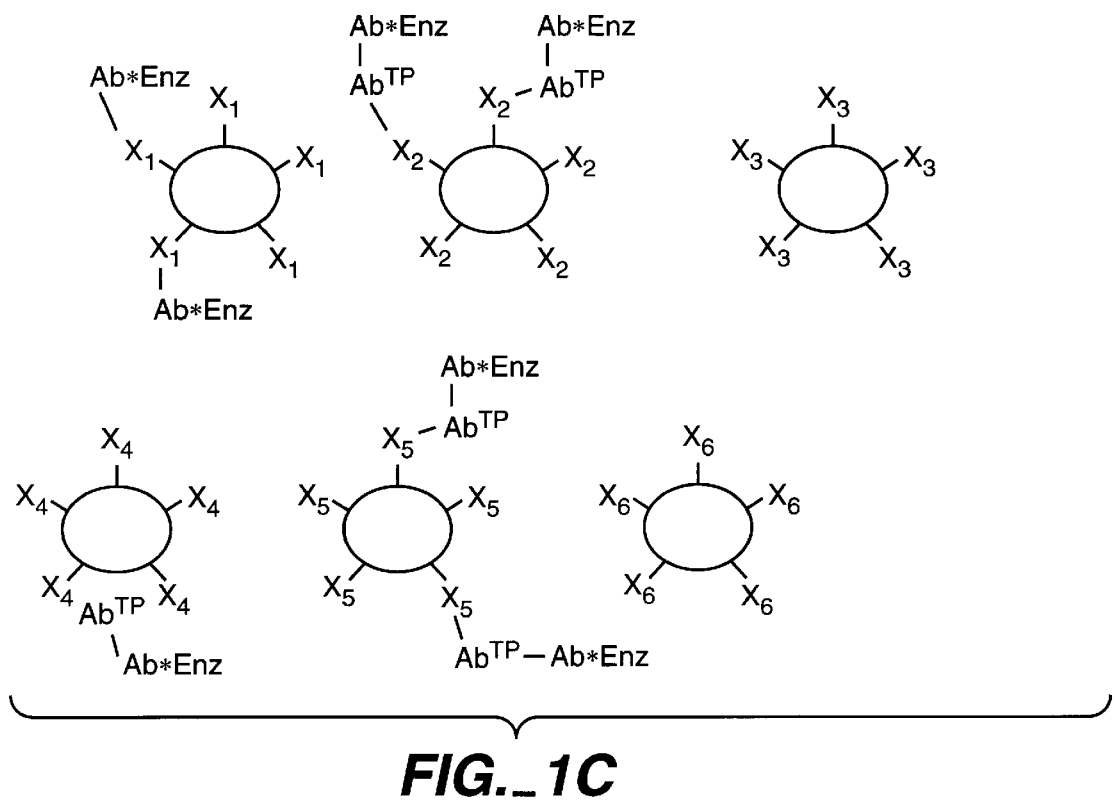
FIG._1C
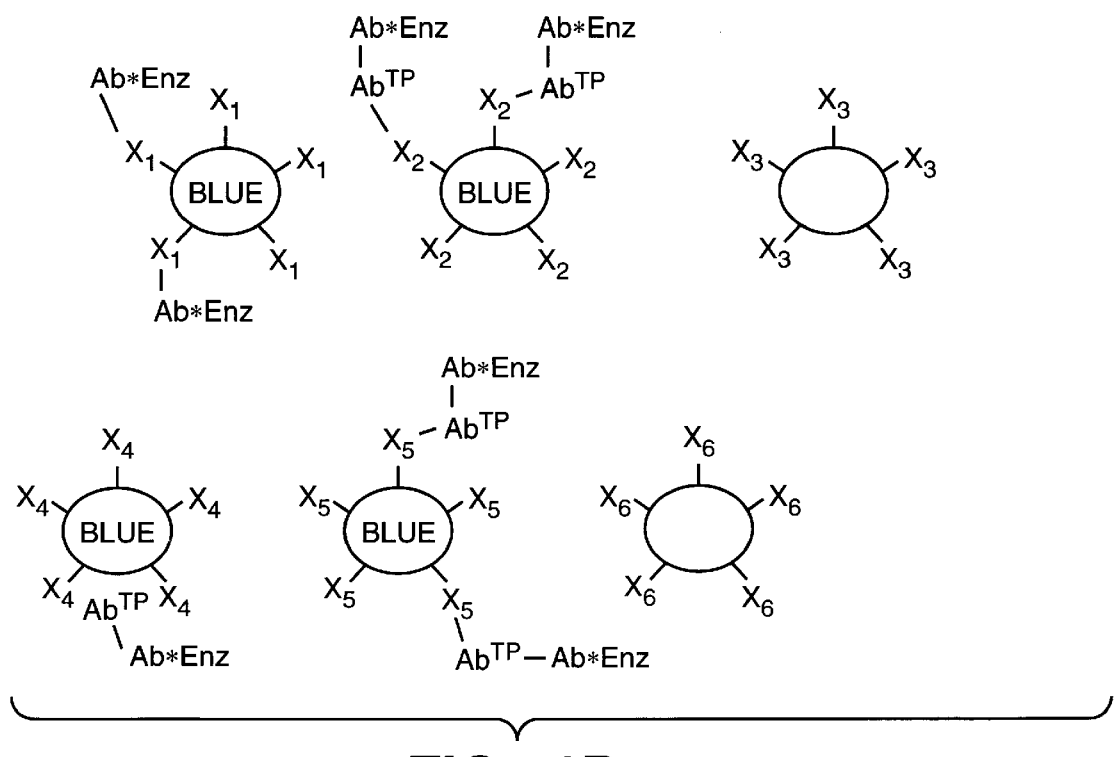
FIG._1D

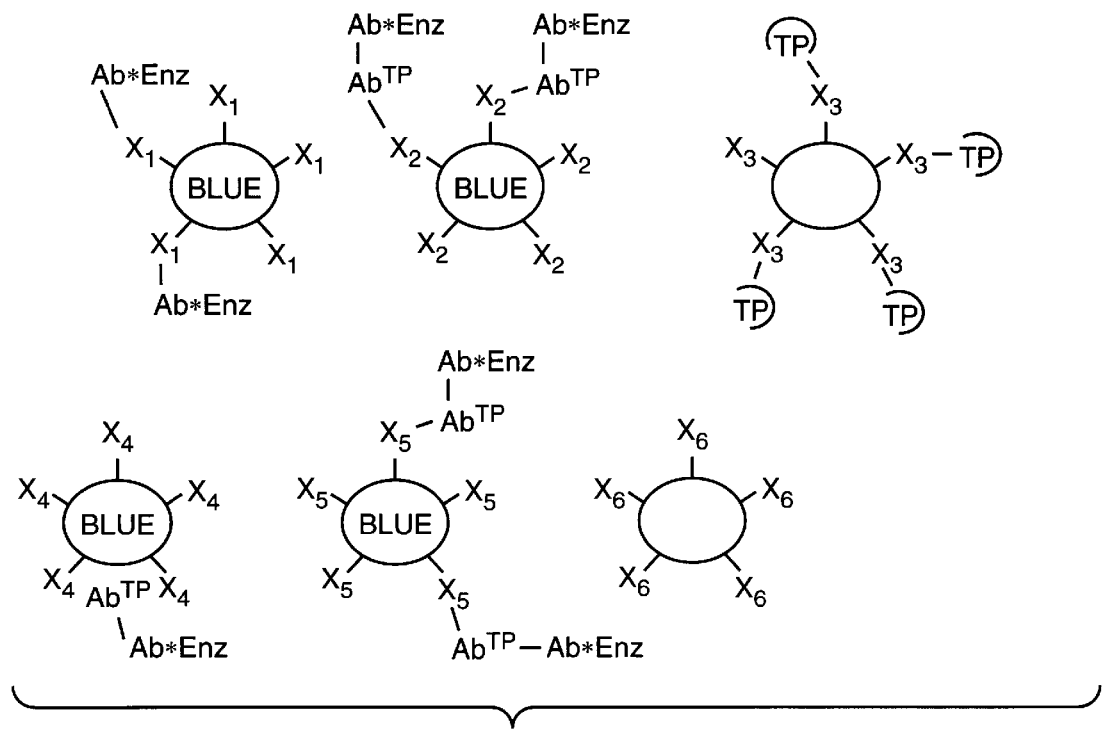
FIG._1E
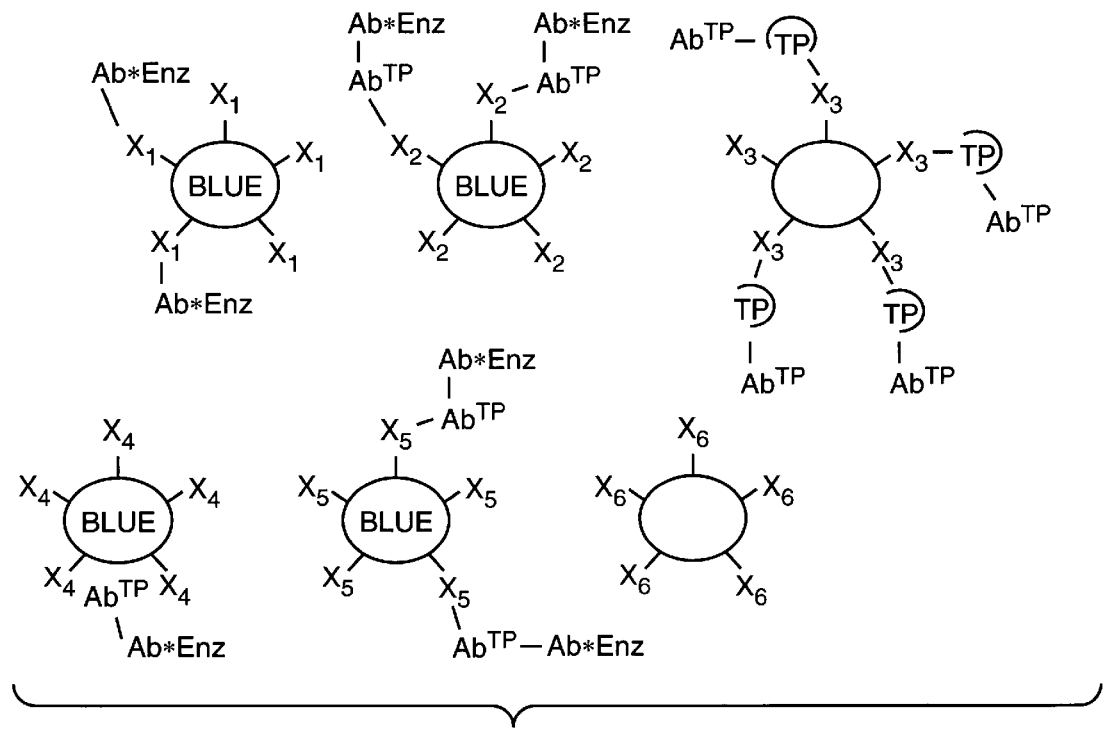
FIG._1F

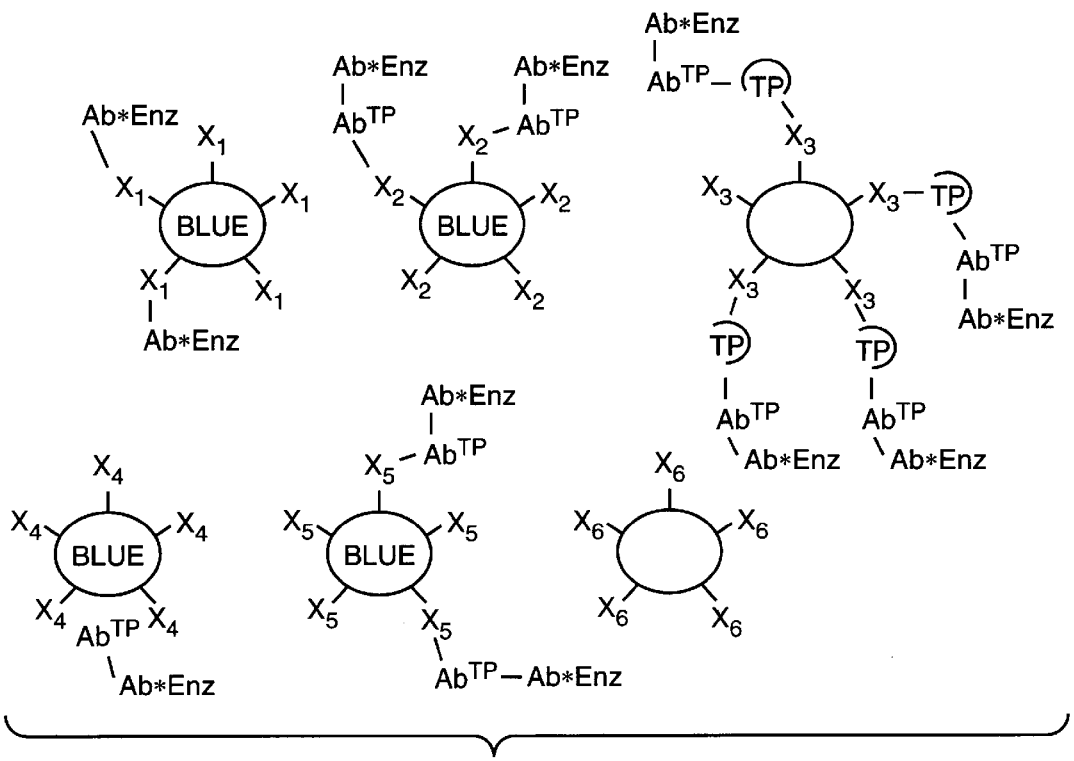
FIG._1G
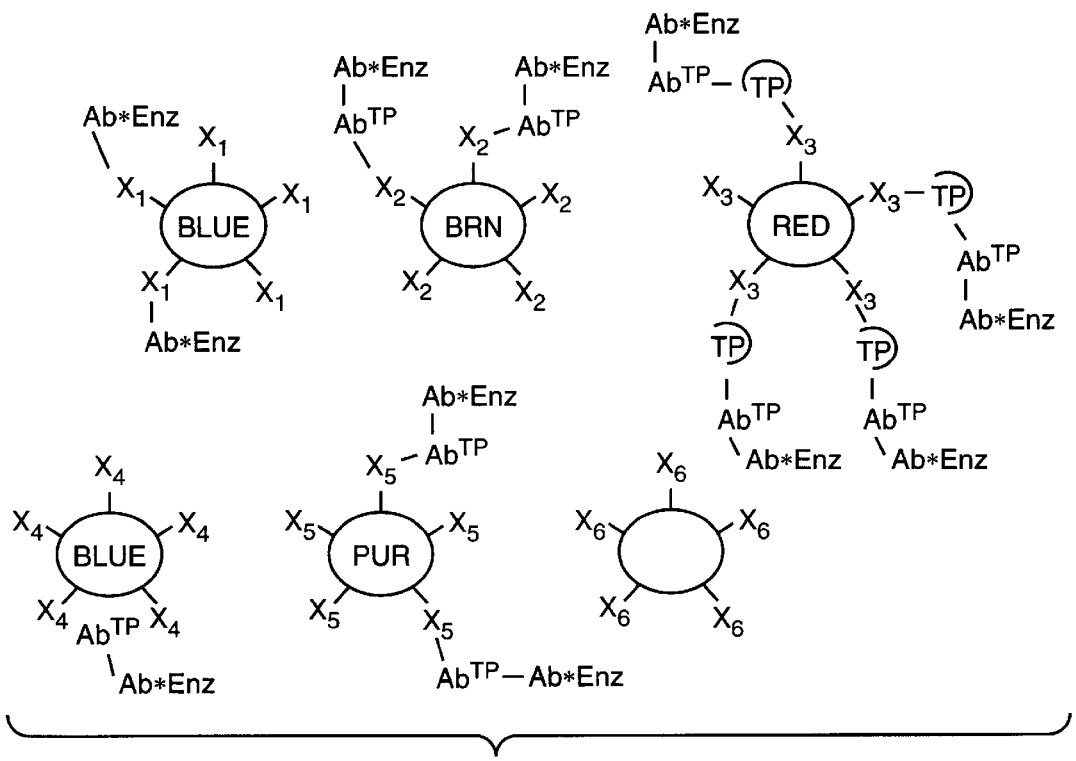
FIG._1H

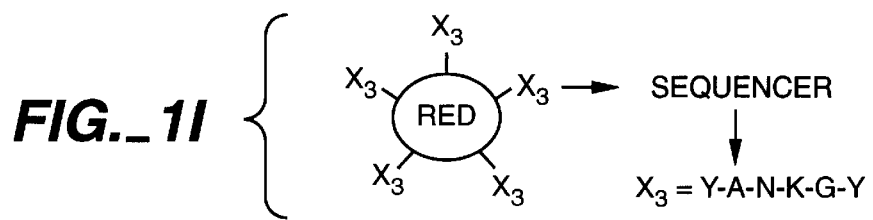
FIG._1I
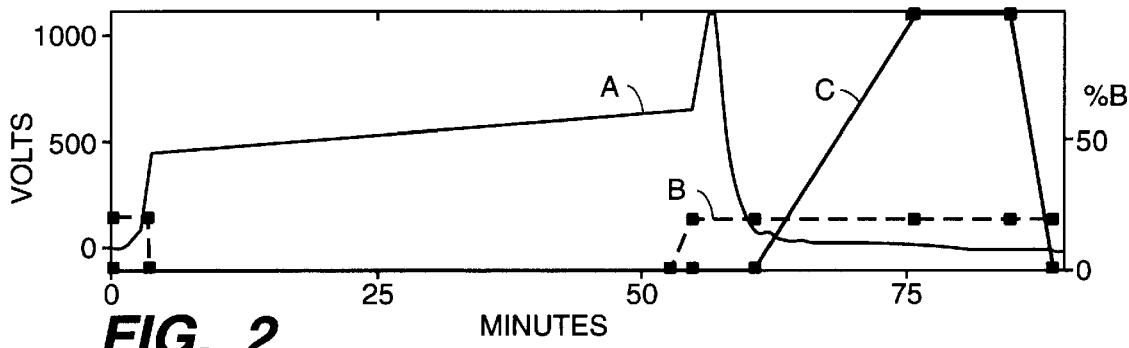
FIG._2
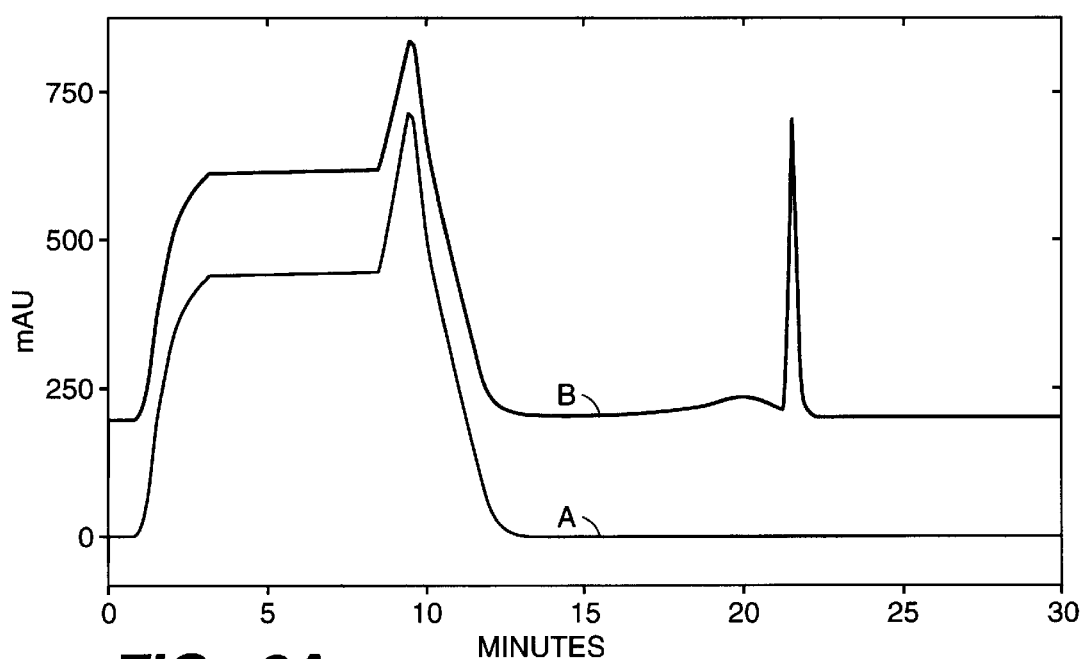
FIG._3A
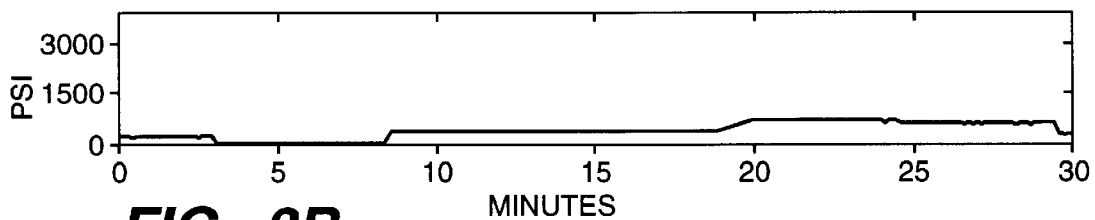
FIG._3B

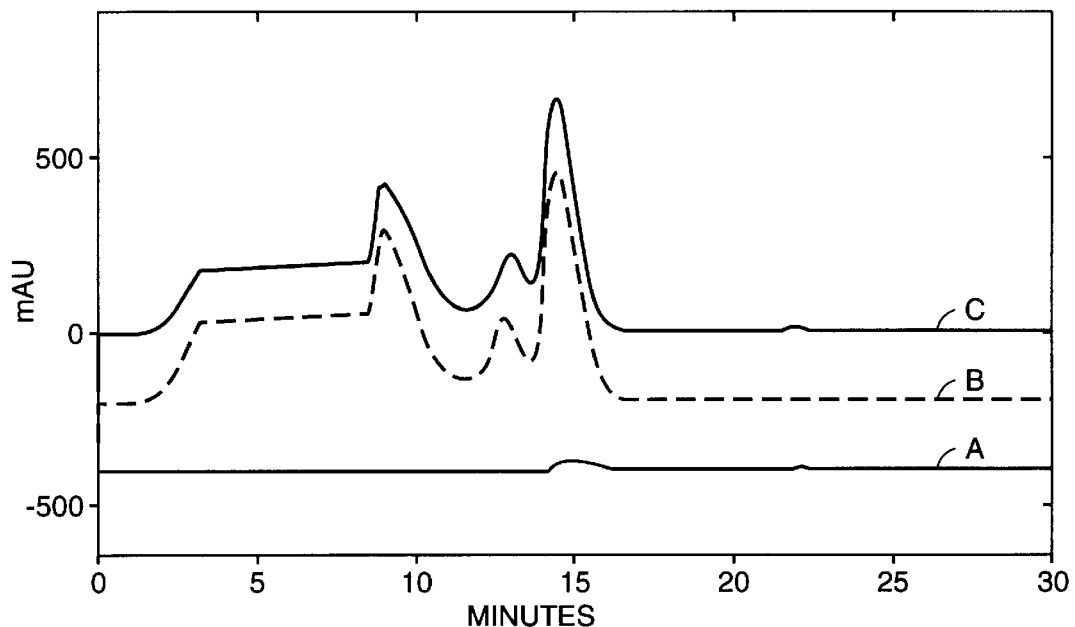
FIG._4A
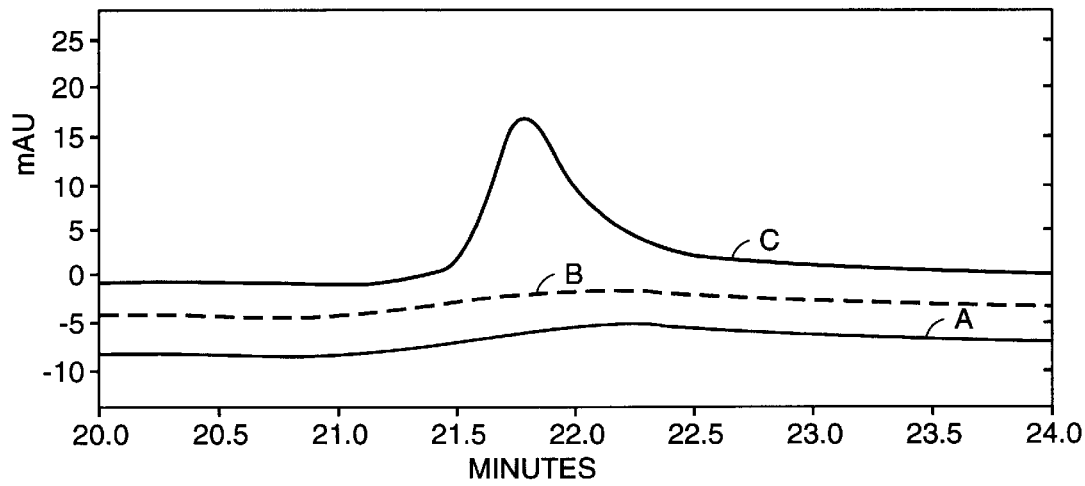
FIG._4B

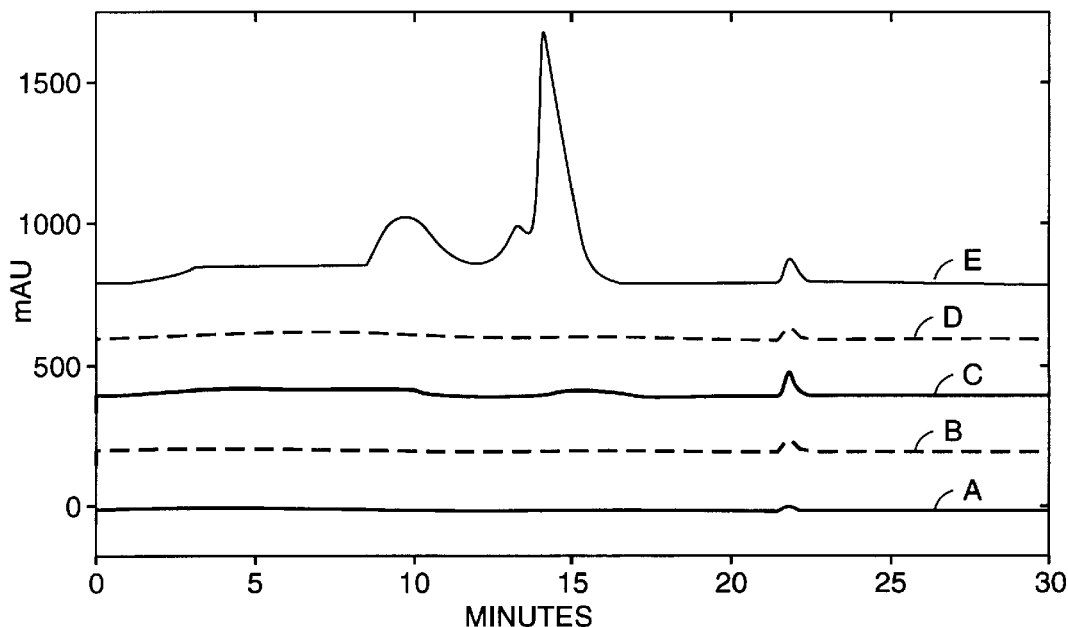
FIG._5
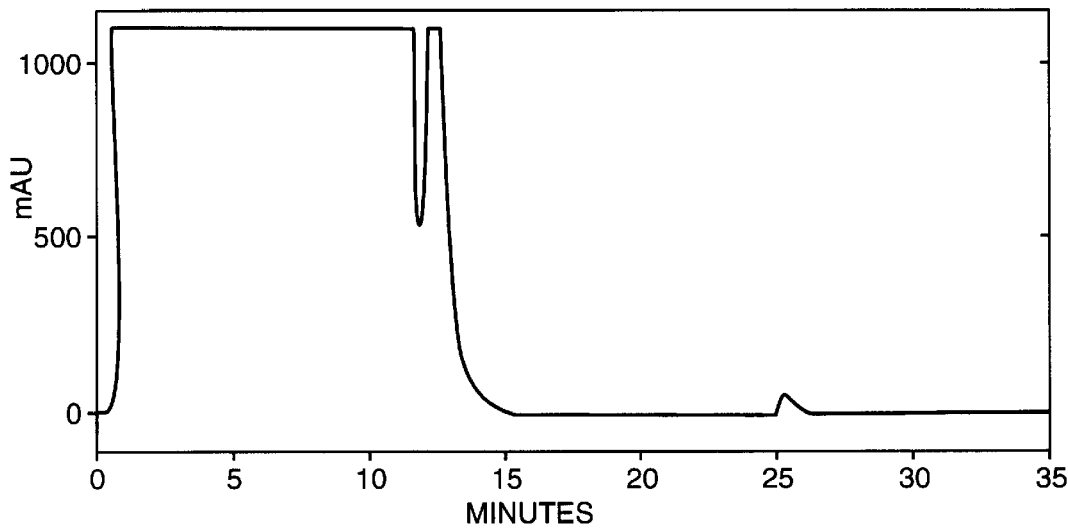
FIG._7A

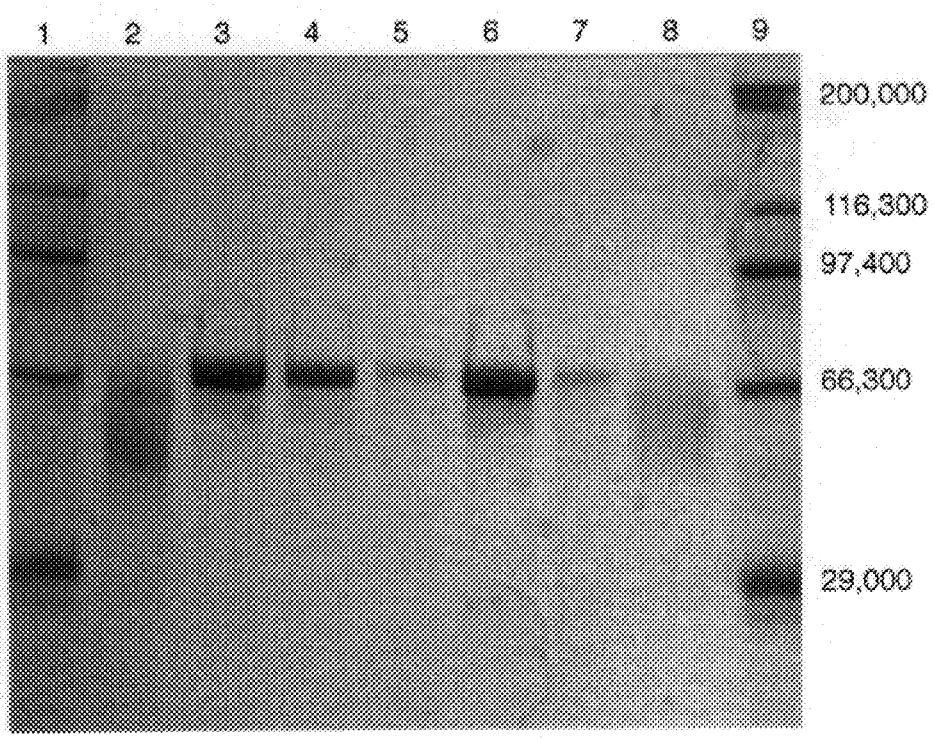
FIG._6A
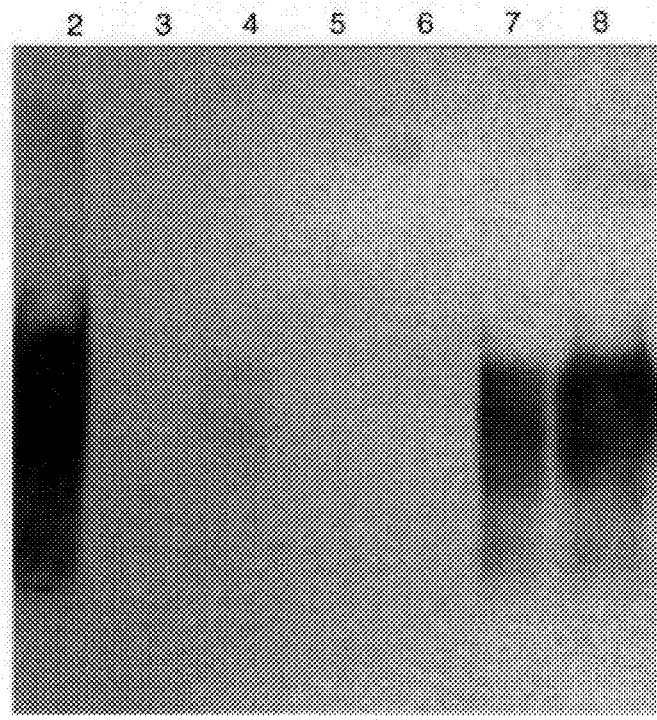
FIG._6B

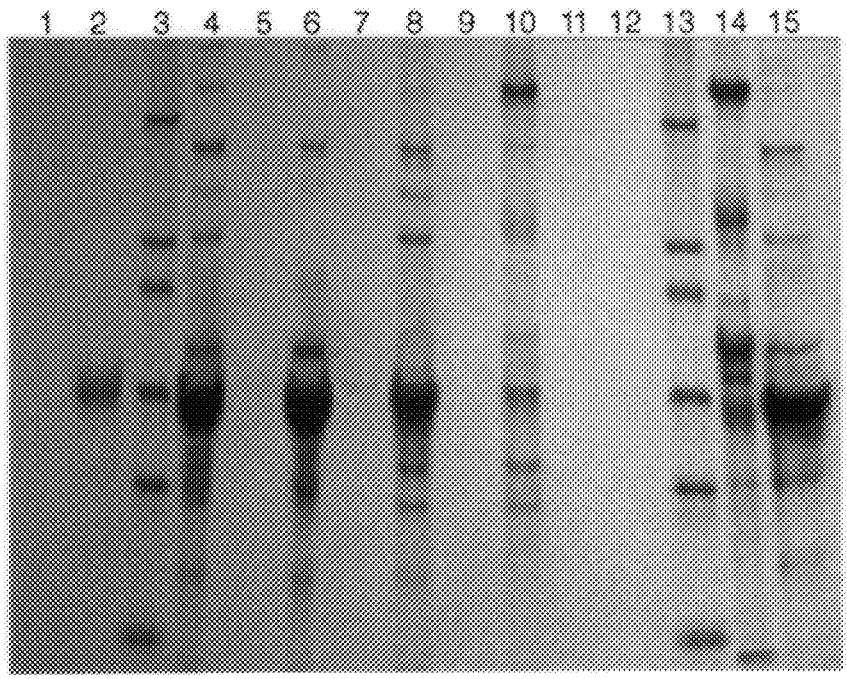
FIG._7A
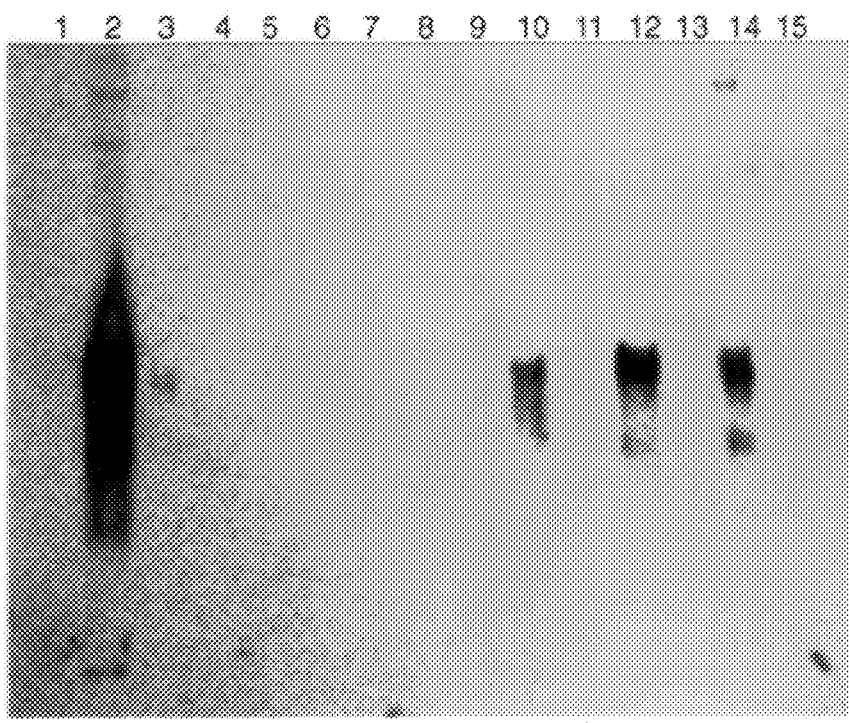
FIG._7B

SCREENING OF COMBINATORIAL PEPTIDE LIBRARIES FOR SELECTION OF PEPTIDE LIGAND USEFUL IN AFFINITY PURIFICATION OF TARGET PROTEINS

RELATED APPLICATION

U.S. patent application Ser. No. 08/210,830 filed Mar. 17, 1994 in the names of D. J. Hammond, et.al., entitled *Random Combinatorial Ligands for Affinity Chromatography of Target Molecule*.

BACKGROUND OF THE INVENTION

1. Field

This invention is concerned generally with a method for the identification of ligands that bind to other molecules, and specifically, an identification method that distinguishes the target-specific ligand by differentiating it from ligands that specifically or non-sepcifically bind with the detection reagents used in the assay.

2. Background

Peptide affinity columns offer substantial advantages over existing chromatography techniques for the purification of proteins (1). The power of this purification methodology, based upon known binding sequences, has been emphasized in the literature (2), but a major limitation has been the lack of known sequences which can act as ligands (1). The recent development of random peptide libraries (also called combinatorial, mimotope or epitope libraries) which contain a vast array of amino acid combinations for peptides of a defined length has allowed a rational approach to characterizing protein-peptide interactions (3–13).

Following the procedure first proposed by Scott and Smith (3), a hexamer (6 amino acid residues) library can be produced by splicing chemically synthesized oligonucleotides of random sequences (of 18 different nucleotide codons) into the coding region of a bacteriophage coat protein. Greater than $10^7$ of the possible $10^{14}$ unique nucleotide codons can be represented with current phage-display technology (3–6). The phage are replicated in host *Escherichia coli* cells, harvested, and then incubated directly with the target protein immobilized on the surface of a culture dish (3). The phage that contain a peptide sequence that specifically interacts with the target protein are immobilized by the target protein while the phage that do not specifically bind to the target protein are lost in subsequent washing. The bound phage are harvested and processed so that the peptide that specifically binds the target protein can be identified.

However, methods for screening combinatorial libraries of ligands for affinity purification have major limitations: 1) phage displaying peptides that bind to the target protein must be isolated by biopanning; 2) the DNA of the binding phage must be sequenced; 3) before binding or purification with the peptides can be assessed, peptides must be synthesized and purified, and then chemical coupling of the ligands onto a chromatographic support must be done; and 4) the microenvironment of the peptide sequence presented on the surface of the chromatographic support may be very different from that presented by the phage which may radically affect the ability of the peptide to bind its target. These limitations have made the use of combinatorial libraries as a source of peptide ligands laborious and the identification of target protein-specific peptides uncertain.

In the mix, divide and couple synthesis first demonstrated by Furka (7), millions of unique peptide sequences are generated on polystyrene-based resinous beads. Subsequent improvements to the technique have allowed one to identify reactive sequences (10). However, identification of target-specific sequences by these binding assays has been compromised by high background staining from inefficient batch washing and the inherent inability to differentiate between sequences on beads that interact with the detection reagents from those that interact specifically with the target protein.

To overcome difficulties in distinguishing which unique peptide (bead) is interacting specifically with the target protein and which peptide (bead) is reacting with the detection reagents, I have synthesized peptides on a hydrophilic chromatographic resin and devised a two-step staining procedure that dyes beads reacting with the detecting reagents one color and those specific for target protein another. Typically this is performed with antibody-enzyme conjugates as the detecting reagents, although other reagents can be used. To create the most efficient washing conditions possible, we perform all assays in high pressure liquid chromatography (HPLC) columns, taking advantage of the flow-through characteristics of the resin. Each reagent is contacted with the beads as a separate HPLC injection with a wash program that removes non-specific binding by a salt gradient. Thus, automation of the assay is effected and run-to-run variations common with batch assays are eliminated.

In addition to the difficulties in identifying peptides that bind specifically to the target protein, the use of chromatographic media capable of providing the support for peptide syntheses and HPLC is limited. Most peptide synthesis supports are polystyrene-based resins that are inappropriate for use with biological assays. It is well known in the literature that polystyrene-based resins exibit both specific and non-specific interactions with various plasma proteins (11). To decrease non-specific binding to the detection reagents, hydrophilic peptide resins have been used in the synthesis and screening of peptides (12,13). Several polystyrene-based peptide synthesis resins have been rendered hydrophilic (8,9); these, however, are designed for chemical synthesis and not for direct biological assays (13), nor as large-scale chromatography supports.

Meldal, et al. have demonstrated the use of a commercially available acrylamide polymer resin modified for peptide library generation (12). Although appropriate for peptide synthesis and probing libraries, acrylamide resins do not have the chemical rigidity necessary for large scale high performance chromatography.

To overcome the problems associated with hydrophobic resins, I have developed a new modified resin which can be used for peptide synthesis, screening, evaluation, and possibly final chromatographic use. The resin forming the basis of this invention is a polyhydroxylated methacrylate polymer commercially available from TosoHaas (14). The distinguishing characteristics of this resin are the inherent hydrophilic nature of the polymer, the large pore size (nominally 1000 angstroms), mechanical and chemical rigidity, and the graded ranges of bead diameters for direct applications in chromatography separations. This resin, after simple modification to generate a free amino group for peptide synthesis, shows good chemical resistance to classical peptide synthesis reagents.

This resin and the two-color staining assay have enabled us to identify peptide sequences that bind target proteins that, in contrast to the prior art, are selected to be specific only for the target protein and not the reagents. Beads binding to the detecting reagents are excluded by my method.

SUMMARY OF THE INVENTION

My invention is a procedure for determining which peptide in a combinatorial peptide library binds specifically with a target protein. The peptide library is bound to chromatographic supports and then incubated with the detecting reagents, resulting in a detectable change (e.g., a color change) of the support where the peptides or the support binds with the detecting reagents. The target protein is then added to the supports under conditions conducive to the target protein binding in a specific fashion to a peptide on the support. Detecting reagents are again added, this time resulting in a different change (e.g., a different color) which distinguishes the target protein bound specifically to the peptide from the prior, first change. In the preferred embodiment the detecting reagents are antibodies and their enzyme conjugates, and the procedure is performed using an HPLC apparatus, which serves as an efficient means for adding reagents and washing unreacted reagents from the system. The identified peptide can then be manufactured and bound to a chromatographic support for use in affinity purification of the target protein. The preferred support is hydrophilic and highly porous, having a preferred average pore size of about 800 to about 1200 angstroms, preferably about 1,000 angstroms. Although a preferred labeled detection system includes an enzyme-conjugated label (tag) which, depending on the substrate chosen, will permit generation of observable color changes, other lables or tags or combinations may be used (e.g. radio-labeled or fluorescentlabeled antibodies).

BRIEF DESCRIPTION OF THE FIGURES

FIGS. 1(A)–1(I): Schematic of the two color immunostaining procedure.

A: Initial population of beads which have polypeptides ($X_{1-6}$) bound to them. The polypeptides on each individual bead have substantially the same sequence. The column is equilibrated by washing with buffers.

B: Add the first antibody ($Ab^{TP}$) and incubate, then rinse. Rinsing removes the loosely bound $Ab^{TP}$; what remains is non-specifically and specifically bound $Ab^{TP}$ on the beads. N.B. $Ab^{TP}$ is an antibody which specifically binds target protein.

C: Add the second antibody which is conjugated to enzyme (Ab*Enz). Incubate, and then rinse. What remains is Ab*Enz bound tightly and specifically to the bound $Ab^{TP}$ and also bound non-specifically and specifically to the beads. N.B. Ab*Enz binds specifically to $Ab^{TP}$.

D: Add the blue dye substrate for the enzyme which dyes the enzyme bound beads a blue color. Incubate, then rinse out the excess blue dye.

E: Add the target protein (TP}). Incubate, and then rinse. The target protein specifically binds to a number of polypeptides among the population of beads.

F: Add $Ab^{TP}$ and incubate, then rinse. The $Ab^{TP}$ specifically binds TP}.

G: Add Ab*Enz. Incubate, then rinse. Ab*Enz specifically binds to $Ab^{TP}$.

H: Add red dye substrate for the enzyme which dyes the enzyme bound beads to a red color. N.B. Any remaining enzyme activity from the first color beads will result in those beads turning purple or brown.

I: Isolate red beads visually and subject single beads to peptide sequence analysis.

FIG. 2: Chromatogram of the immunoassay technique for Ribonuclease S (RNase S) protein injected on the YNFEVL-TSK resin diluted (1:20 w/w) with TSK-Blank. The upper line (A) is the absorbance at 280 nm; the middle line (B) is the flow rate, and the lower line (C) indicates the gradient conditions.

FIGS. 3(A) and 3(B): Validation of the HPLC Affinity assay by RNase S protein and peptideresin (YNFEVL-TSK). The top figure shows the 280 nm absorbance profile for Human Serum Albumin (HSA) (A) and RNase S protein in HSA (B). The bottom figure is the pressure tracing from chromatogram B.

FIG. 4A: Chromatograms of Factor IX binding to YANKGY-TSK. The bottom trace (A) is a buffer blank. The middle trace (B) is the carrier protein (1.0 mL of 0.5% HSA). The top trace shows that 55 μg of Factor IX injected onto the column is released during the acid wash.

FIG. 4B: This figure shows the Factor IX peak from the chromatogram in FIG. 4A at increased scale.

FIG. 5: Chromatograms of various amounts of Factor IX injected onto YANKGY-TSK. The bottom trace (A) is 55 μg of Factor IX without HSA. Trace B is 110 μg of Factor IX and C is 220 μg Factor IX, both without HSA. The D trace is 220 μg of Factor IX heated at 95° C. for 5 min prior to injection. The top trace (E) is 220 μg Factor IX in HSA.

FIGS. 6(A) and 6(B): SDS-PAGE (FIG. 6A) and Western blot (FIG. 6B) of mixtures of Factor IX and HSA. Lanes 1 and 9 are molecular weight standards. Lane 2 is Factor IX (Enzyme Research Labs; South Bend, Ind.). Lane 3 is an HSA standard (Miles Inc.) Lane 4 is the starting material that was injected onto the YANKGY-TSK affinity column (1.0 ml, 220 μg of Factor IX in HSA). Lane 5 is the first flow-through peak. Lane 6 is the second flow-through peak. Lane 7 is the NaCl wash. Lane 8 is the acid eluted peak. Approximately 10 μg of total protein was loaded into each lane.

FIGS. 7(A) and 7(B): Chromatogram (FIG. 7A), SDS-PAGE (FIG. 7B) and Western blot (FIG. 7C) of 1.0 ml citrated human plasma on the Acetyl-YANKGY-TSK resin. Approximately 10 μg were loaded in each lane and the electroblotted gel was loaded with the same amount of sample as the Coomassie stained gel. Lanes 1, 5, 7, 9, and 11 were blank. Lane 2: 1.0 μg of Factor IX; Lane 12: 0.0625 μg of Factor IX. Lanes 3 and 13: molecular weight standards. Lanes 4 and 15: human plasma. Lane 6: flow through (t=0 to 12 min); Lane 8: flow through (t=12 to 15 min). Lane 10: the acid eluate. Lane 14: a partially-purified Factor IX intermediate. The Western blot on the lower right shows no Factor IX in the starting material or flow throughs. A strong immuno-detected band corresponding to the Factor IX zymogen is in the acid eluate.

SPECIFIC AND PREFERRED EMBODIMENTS

Materials and Methods

Resin Chemistry For peptide synthesis, a polyhydroxylated methacrylate-type chromatography resin, preferably Toyopearl 650M Chelate (65 μm particle size, 1000 Å pore size; TosoHaas, Montgomeryville, Pa.) was rinsed in a 25 g reaction vessel with water, methanol and dimethylformamide (DMF). A five-fold molar excess of ethylenediamine over resin carboxylate was coupled onto the carboxylate moiety with a slight molar excess of benzotriazole-1-yl-oxy-tris-pyrrolidino-phosphonium hexafluorophosphate (PyBOP, Novabiochem, La Jolla, Calif.) and N-methylpyrrolidinone (NMM, three-fold molar excess over PyBOP; Aldrich Chemical Co.; Milwaukee, Wis.) in DMF for 60 minutes. The aminated resin was washed with DMF, then methanol, then dried in vacuo.

To generate a non-cleavable resin, two standard solid phase peptide synthesis couplings followed to introduce two molecules of β-alanine (Novabiochem) spacer residues (referred to as TSK-Blank). To generate a cleavable resin for soluble peptides a two-fold molar excess (over amine on the beads) of p-[(R,S)-α-[1-(9H-Fluoren-9-yl)-methoxyformamido]-2,4-dimethoxybenzyl]-phenoxyacetic acid (Novabiochem) was activated with a slight molar excess of PyBOP and NMM, then added to the aminated TSK-Blank resin. Coupling was allowed to proceed for 4 hours, with subsequent DMF and methanol washes. Other linkage chemistries, which are widely known by those practiced in the art, and are compatible with the functional moieties available on different polyhydroxylated methacrylate resins, can be used. A commercially available Rink amide resin was used for comparison.

Combinatorial Library Peptide Chemistry Combinatorial peptide libraries were generated in a manner similar to Furka (7). A large-scale synthesis block in the multiple peptide synthesizer was used to perform each coupling in a semi-automated manner. One-half gram of dried, aminated TSK-Blank resin was added to each of 18 reaction vessels and 18 of the 20 naturally occurring L-amino acids (in this embodiment I omitted cysteine and methionine; however, this is not a requirement for the utilization of this invention) were coupled by standard FMOC chemistry (see below). The resin from each vessel was pooled and washed in DMF with argon agitation. The resin was equally redistributed into the 18 reaction vessels and the next amino acid was coupled as the first. This was repeated until the hexamer library was complete (two working days). The resin was pooled, washed with methanol, dried in vacuo, then deblocked with Reagent R (18) (90% trifluoroacetic acid (TFA), 5% thioanisole, 3% ethanedithiol, 2% anisole; all from Aldrich) for 3 hours with argon agitation. The resin was washed with 20 column volumes of methanol, then dried in vacuo.

Batch Peptide Synthesis Peptide sequences were synthesized by the solid phase method (15) on a Gilson AMS422 Multiple Peptide Synthesizer (16) with FMOC as α-amino protection (16,17). Depending on whether or not the peptides would be cleaved from the beads for analysis, either the aminated-cleavable TSK-Blank resin, or the non-cleavable TSK Blank resin, or the Rink resin (for comparison) were used as the synthesis support. Large scale single couplings of amino acids (5-fold molar excess; 1 mL of 0.5M in DMF) were activated in situ with PyBOP (0.5 mL of 0.3M in DMF) and NMM (0.25 mL of 1.19M in DMF) with our modified TosoHaas resin (0.3 g, 200 μmoles) or Rink amide resin (0.5 g, 200 μmoles). Coupling was allowed to proceed with argon bubbling agitation for 45 minutes. All peptides were cleaved and/or blocked with Reagent R for 3.5 hours.

For affinity chromatography analysis, the TSK non-cleavable resin-peptides were deprotected (as generally practiced in the art) in the synthesis vessel, extensively washed with methanol and dried in vacuo. For peptide analysis, the TSK cleavable and the Rink peptide-resins were cleaved and deprotected in 20 mL scintillation vials. These peptide mixtures were filtered away from the resin directly into 40 mL cold anhydrous diethyl ether (Aldrich) through a medium porosity sintered glass funnel. The filter cakes of peptides were dissolved in 50% acetonitrile/water and lyophilized in a tared scintillation vial. These precipitated, unpurified peptides were dissolved at 25–50 mg/mL in 50% acetonitrile/water and 1 mL was purified by preparative HPLC (Gilson, Inc.) with a 22 mm×250 mm (C18 15 u 300 Å) reverse phase column (Vydac; Hesperia, Calif.). To ascertain purity, crude peptides were dissolved at 10 mg/mL in 50% acetonitrile/water and purified peptides were dissolved at 10 mg/mL in 20% acetonitrile/water. 10 μL aliquots were analyzed by microbore HPLC (Ultrafast Microprotein Analyzer, Michrom BioResources, Inc.; Sacramento, Calif.) with a 2.1 mm×150 mm C18 5u 300 Å reverse phase column and a 2 to 60% acetonitrile gradient in water over 12 minutes.

Analyses Amino acid analysis was performed as described by Spackman (20) with a 6300 Amino Acid Analyzer (Beckman Instruments, Inc.; Fullerton, Calif.) using ninhydrin detection. Peptide mass determinations were performed by positive ion fast atom bombardment (FAB) ionization on a JEOL HX-110 double focusing mass spectrometer. The peptides were spotted in 50% acetonitrile/water onto a thioglycerol matrix. The mass range scanned depended upon the expected mass of the peptide. Peptide sequencing was performed by Edman chemistry using an ABI 477A Protein/Peptide Sequencer (Applied Biosystems; Foster City, Calif.) interfaced with a 120A HPLC (C18 PTH, reverse-phase chromatography) Analyzer to determine phenylthiohydantoin (PTH) amino acids. Sandwich ELISAs were performed as described by Bessos (21). Protein samples were quantitated by the Biuret assay (22), then analyzed by SDS-PAGE (23) and Western blot techniques (24).

HPLC Library Immuno-Assays To differentiate between detecting reagent-binding and target-binding peptide-resin beads, we developed a two color peptide library staining chromatography technique. FIG. 1 is a schematic of the preferred embodiment of the technique. All assays were performed on an Ultrafast Microprotein Analyzer in a 2.1 mm I.D.×150 mm long stainless steel column (volume=520 μL) at 37° C. Dry library resin was packed into the column by vacuum, then the column was attached to the detector flow cell and washed with 20 column volumes of 20% methanol/water, 5 column volumes of 100% Buffer A (10 mM HEPES, 100 mM NaCl, 2.5 mM $CaCl_2$, 20 mg/mL D-mannitol; all from Sigma Chemical Co.; St. Louis, Mo.), then 5 column volumes of 50% Buffer B (Buffer A with 1.0M NaCl) to clean the resin. The complete assay comprised of seven chromatography injection programs sequentially linked and executed as a batch (EXChrom Chromatography Data System, Scientific Software, Inc.; San Ramon, Calif.). Each injection program was 90 min long. At the start of each injection program, a 1.0 mL sample loop of reagent was injected at 200 μL/min for 3.5 min, then allowed to perfuse the column at 5 μL/min for 50 min before the flow increased to 400/μL/min for the duration of the run. At 60–75 min, a salt gradient from 0.1M to 1.0M NaCl eluted non-specific binding proteins. This high salt buffer was used to wash the column for 15 min, then the column was re-equilibrated to the original conditions.

For each assay batch there were 7 injections: 1) Buffer A blank; 2) 0.5% Human serum albumin (HSA; Miles, Inc., Clayton, N.C.) without target protein (FIG. 1A); 3) 1:1000 diluted first antibody (FIG. 1B); 4) 1:1000 diluted second antibody-alkaline phosphatase conjugate (FIG. 1C). Each immunoreagent was diluted in 0.5% HSA in Buffer A. After the fourth injection program, the batch job was stopped for the first staining process. In this particular example, the buffer flow was stopped, the column disconnected and the resin extracted with 100% Buffer A at 300 μL/min. 15 fractions (2 drops per fraction) were collected into a 24 well microtiter plate (Corning/Costar).

BCIP/NBT was added and the staining performed in the well. Visual observation of the staining process allowed for optimal staining times. Alternatively, the staining can be accomplished in the column, making the entire procedure fully automated (FIG. 1D). The stained resin fractions were loaded into 3 mL reaction tubes, washed extensively with water, dried in vacuo, then dry packed back into the column in the same order the resin was fractioned. TSK-Blank resin was used to fill the column outlet to replace any lost resin. After re-equilibrating the column, target protein (2.4 pmole sample amount in Buffer A with 0.5% HSA) was injected (injection program number 5) (FIG. 1E). The following two injection programs, 6 and 7, were the same as program numbers 3 and 4 (FIG. 1F & 1G). After these programs were complete, the resin beads were fractionated as before, then stained with Fast Red in the microtiter plate wells and inspected visually.

Affinity Purification of Target Protein Affinity purification of target protein was used to assess the ability to purify proteins with the peptide sequences identified as being specific. Individual library-derived sequences that were found to bind to target proteins were synthesized in a batch format on TSK-Blank resin as described above. The deprotected peptide-resin was dry packed into a blank column as described above and washed with 20 column volumes of 20% methanol/water, then 10 column volumes of Buffer A, and assayed by sequential 1.0 mL injections of 1) Buffer A blank, 2) 0.5% HSA, and 3) target protein in 0.5% HSA. Non-specifically bound proteins were washed off the column in a step gradient of 1.0M NaCl for two column volumes, and the target protein was eluted from the column in a weak acid solution.

Validation of the HPLC Library Immunoassay

Ribonuclease S protein In this embodiment, the HPLC assay was validated by the use of a control binding peptide for a specific target protein. The previously identified RNase S protein-binding peptide (25), YNFEVL, was synthesized on TSK-Blank resin as taught in the previous section, then diluted with TSK-Blank until the final ratio of peptide-resin to TSK-Blank was 1:20 of the total weight. FIG. 2 shows the microbore HPLC injection program of the UV trace, flow profile and gradient conditions of the immunoassay technique using RNase S protein as the target protein (HSA is the protein carrier). Red beads (indicating target protein interacting with the YNFEVL-TSK resin beads) were found at the frequency of 5% throughout the column demonstrating the column is not depleted of target or immunoreagents during the peptide library immunostaining chromatography runs. Also present were clear white beads from the TSK-Blank which showed no reactivity with the detection system or the RNase S protein. Dark blue beads which indicate non-specific or immunoreagent-specific interactions were present only at a very low frequency (less than 0.01%). Some beads became chipped or scored during the process of syntheses, cleavage, or chromatography analysis, but in general, the integrity of the beads as a chromatography support did not appear to be compromised as the beads did not collapse upon high pressures (greater than 4,000 psi).

Validation of the HPLC Affinity Chromatography Method

Ribonuclease S Protein Affinity Chromatography In this embodiment the HPLC affinity methodology is validated by the previously described RNase S protein/YNFEVL peptide system. Peptide synthesis was performed as taught in the previous section. FIG. 3 shows the HPLC affinity chromatography analysis of RNase S protein. 42 nmoles of RNase S protein was injected in a 1.0 mL volume onto the column at 200 µL/min for 3 min. The flow was decreased to 5 µL/min for 5 min to perfuse the column, then increased to 400 µL/min to wash off the unbound protein. At 13 min, an injection of 1.0 mL Buffer A with 1.0M NaCl eluted non-specific binding proteins, then the column was returned to 0.1M NaCl until 19 min when a steep gradient to 2 % acetic acid in water and a flow of 800 µL/min began. After 5 min, the column returned to Buffer A to equilibrate the resin. The peak at 22 min represents the target protein eluted in the acid wash.

EXAMPLE

Hexamer Library-Factor IX Target A hexamer peptide library was assayed with the this peptide library immunostaining chromatography assay for its ability to bind the serine protease Factor IX zymogen. The library was assayed as described and several red bead sequences were found. Individual stained beads were hand picked with a pipette under a dissecting microscope. Of the 6 beads isolated from two independent analyses, two beads gave a clear sequence (YANKGY and YNYFNQ). The amount of peptide per bead was found to be approximately 10 pmoles (0.1 meq/g), which is sufficient for sequencing.

Factor IX/Albumin Affinity Purification The library-derived peptide identified above binds and purifies a mixture of a commercially available, highly purified Factor IX zymogen in a solution of human serum albumin. The YANKGY sequence was batch synthesized as described and quantitative amino acid analysis showed the proper sequence. This peptide-resin was tested for its ability to bind Factor IX. FIG. 4 shows the chromatograms, demonstrating that the YANKGY peptide ligand synthesized on the TSK-blank does bind Factor IX. HSA bound to the column to a small extent. However, this was eluted by the salt wash as evidenced by the absence of a peak during the acid elution. In contrast, when Factor IX was added to the HSA, there was a distinct peak eluted by the acid. This demonstrates that the target protein (Factor IX) bound the peptide with sufficient avidity to indicate specificity.

FIG. 5 shows the chromatograms for increasing amounts of Factor IX added to the column. A direct correlation was seen between the acid peak area and the amount of Factor IX injected. Heating Factor IX for 5 min decreased binding to the column, as demonstrated by the decrease of the acid peak area. The top chromatogram in FIG. 5 shows the UV trace of 220 µg of Factor IX in HSA. The acid peak area from this run (FIG. 6, lane 5) was not significantly different in peak area to that of Factor IX without HSA (FIG. 6, lane 3), consistent with the Factor IX being separated from HSA. Aliquots of fractions taken from this run were assayed for Factor IX detection by ELISA (data not shown). No Factor IX was detected in the flow through peak (from FIG. 5, top trace); 17% of the amount of Factor IX injected was detected in the NaCl peak; and 25% in the acid peak. Factor IX may be partially denatured during the acid elution which could account for the lack of full recovery based on ELISA results. Indeed, controls of adding acid to Factor IX prior to analysis in the ELISA do show a 40 to 50% decrease in the ELISA signal. The remainder of the fractions were precipitated in cold (−20° C.) acetone and analyzed by reducing SDS-PAGE, normalizing sample to total protein. FIG. 6 shows that there is a clear purification of Factor IX from HSA. Binding of Factor IX to the YANKGY-TSK column was confirmed by Western blot analysis: a very light Factor IX band was seen in the starting material and no detectable Factor IX was seen in either flow-through fraction but dark bands corresponding to Factor IX were seen in both the NaCl wash and the acid peak.

Plasma-Derived Factor IX Affinity Chromatography The relevance of this library-derived peptide ligand is to purify human Factor IX zymogen from unpurified human plasma. A 1.0 ml injection of human citrated plasma was contacted with an acetyl-YANKGY-TSK column in the manner taught in the above example. Flow through and acid peaks were collected on ice and immediately assayed for total protein, SDS-PAGE and Western blot analyses. FIG. 7 shows the purification chromatogram, SDS-PAGE and Western blot of the fractions collected. Samples were normalized to total protein as described before. There are numerous protein bands in the starting material, the predominant being albumin. The Factor IX band is not visible in any fraction in the Commassie stained gel. The blot shows no Factor IX in the starting material (it is below the sensitivity of the detection system), no Factor IX in the flow through, yet a very large band in the acid peak. With one pass over the YANKGY-TSK affinity column, analyzing total protein and by Western blot, the approximate purification was 200 fold from plasma. This demonstrates conclusively that this library-derived sequence binds and purifies the Factor IX zymogen from human plasma.

Other Detection Systems for this HPLC Assay

Noncolorimetric detecting systems. It can be further appreciated by those skilled in the art that the invention can easily be extended to use different reagents which are functionally equivalent to those used in previous examples. Antibody-conjugates are the preferred embodiment; however, target-enzyme direct conjugates can also be used with this technique. It is well known in the art that the peptide sequence HPQ will bind streptavidin. If this sequence were contained in a peptide library it could be identified by this two color library staining chromatography technique. In this example the third injection should contain some kind of labelling molecule capable of imparting color to the bead (like a phosphatase molecule). The column would be extracted, and the first color reagent (NBT/BCIP) would be applied to the beads. The column would be repacked as described before, and the target injection would be streptavidin conjugated to phosphatase. With subsequent addition of the differential staining reagent (Fast Red) the beads stained the second color would be specific for the streptavidin target.

Moreover, the staining reagent does not have to be an enzyme. Any tag that imparts a signal could be utilized to differentiate the ligands that react with the detecting system from those that react with the target. For example, fluorescent molecules imparting different colors could be used with identification by fluorescence-activated cell sorting; radioactive isotope tags (125I/131I or 35S-Met/75Te-Met) could be identified in autoradiograms or by scintillation counting; or non-radioactive isotope tags (e.g. 14N/15N) could be identified by NMR; or mixed mode color identification where the beads interacting with the detecting reagents are colored as described above and the target-specific beads are identified by luminescence with disodium 3-(4-methoxyspiro(1,2-dioxetane-3,2'-(5' chloro) tricyclo (3.3.1.13,7) decan)-4-yl) phenyl phosphate (CSPD, Tropix, Bedford, Mass.) or any other luminescing reagent.

CONCLUSION

In conclusion, a method has been developed that can quickly identify combinatorial library-derived sequences that are target specific. This two color, peptide library immunostaining chromatographic analysis has been used to identify sequences that bind to the coagulation cascade Factor IX zymogen. The technique has been validated using a peptide sequence which is known to bind Ribonuclease S protein. This technique has further been extended to use the identified peptide ligand to construct an affinity chromatography medium for the purification of the target protein.

This method lends itself to additional useful experimental schemes. By using a strategy of combinatorial resin modification with this two color, peptide library immunostaining chromatographic analysis, chromatographic substrate modifications useful for separations of molecules of similar structure (e.g., isoforms of proteins, or the same proteins from different sources, such as sheep alpha 1 proteinase inhibitor from transgenic human alpha-1 proteinase inhibitor expressed in the sheep's milk) can be identified. In these examples an isoform of the target molecule may be included in the first half of the assay to generate the first color. The different isoform may be included in the second half of the assay to generate the second color. Thus, specificity for the second isoform would be identified by the beads dyed by only the second color.

Binding interactions are important pharmacologically, thus this strategy can be useful for lead identification in drug discovery. For example, a peptide library may be probed with soluble cellular receptors like the soluble form of the epidermal growth factor receptor or the soluble form of the erythropoietin receptor to identify peptide ligands of potential pharmacological significance. A large pore size of the resin is necessary in order to provide full access to the peptide for these large proteins. The method also may be used to identify binding interactions between other kinds of (i.e. non-peptidic) molecules. We have also found this method useful for quick evaluation and optimization of ligands derived from screening phage libraries.

The above examples are intended to illustrate the invention and it is thought variations will occur to those skilled in the art. Accordingly, it is intended that the scope of the invention should be limited only by the claims below.

REFERENCES

1. Baumbach, G. A., Hammond, D. J., Biopharm. 5 24 (1992)
2. Huang, P. Y., Carbonell, R. G., Biotechnol. and Engin., in press
3. Scott, J. K., Smith, G. P., Science 249 386 (1990)
4. Devlin, J. J., et al., Science 249 404 (1990)
5. Cwirla, S. E., et al., PNAS 87 6378 (1990)
6. Folgori, A., et al., EMBO 13 2236 (1994)
7. Furka, A. et al., Int. J. Pept. Protein Res. 37 487–493 (1991)
8. Zalipsky, S., et al., in *Peptides: Structure and Function, Proceedings of the Ninth American Peptide Symposium* (Deber, C. M., Hruby, V. J., & Kopple, K. D. eds.), p.257. Pierce Chemical Co., Rockford, Ill. (1985)
9. Bayer, E., Rapp, W., *Chemistry of Peptides and Proteins* 3 (Ovchinnokov, Y. A., Ivanov, V. T., eds.)
10. Lam, K. S., et al., Nature 354 82–84 (1991)
11. Boisson-Vidal, C., et al., Biomedical Materials Res., 25 67–84 (1991)
12. Meldal, M., et al., Proc. Natl. Acad. Sci. USA 91 3314–3318 (1994)
13. Vagner, J., et al., *Innovative Perspectives in Solid Phase Synthesis* (Epton, R., ed.), in press
14. Kato, Y., et al., J. Chromatography 354 511–517 (1986)
15. Merrifield, R. B., Fed. Proc. 21 412 (1962)
16. Gausepohl, H., et al., Peptide Research 5 315–320 (1992)
17. Atherton, E., et al., J. Chem. Soc. Chem. Commun. 539–540 (1978)
18. Fields, G. B., et al., Int. J. Pept. Prot. Res. 35 161 (1990)

19. Albericio, F., et al., J. Org. Chem. 55 3730–3743 (1990)
20. Spackman, D. H., et al., Anal. Chem. 30 1190 (1958)
21. Bessos, H., et al., Thrombos. Res. 40 863 (1985)
22. Davis, E. M., Am. Biotech. Lab., Jul. 28 (1988)
23. Laemmli, U. K., Nature 277 680 (1970)
24. Bowen, P., et al., Nuc. Acids Res. 8 1 (1980)
25. Smith, G. P., et al., Gene 128 37–42 (1993)

What is claimed is:

1. In a method of selecting a ligand which will bind to a target substance, the ligand being from a random ligand library, wherein the ligands of the random ligand library are immobilized on individual support materials, and wherein binding of the target material to a ligand on an individual solid support is detected by means of a color-generating detection system, the improvement comprising incubating the population of random ligands with components from the detection system to generate a first color, thus detecting those ligands which bind to the components of the detection system, and then adding the target substance to the population of random ligands and the components of the detection system, such that the detection system is now used to generate a second, different color, thus allowing for detection of ligands which bind to the target substance against the background of random ligands which bind to the components of the detection system.

2. The method of claim 1 wherein said color-generating detection system comprises an enzyme-conjugated tag.

3. The method of claim 2 wherein the tag is an antibody.

4. The method of claim 1 wherein the ligand is a peptide and the target substance is a protein selected from plasma proteins and proteins expressed from a genetically engineered cell or hybridoma.

5. The method of claim 4 wherein the peptide comprises about 3 to 10 amino acid residues.

6. The method of claim 4 wherein the protein is Factor IX.

7. The method of claim 1 wherein the support material is a resin.

8. The method of claim 7 wherein the support material is hydrophilic.

9. The method of claim 7 wherein the support material is porous.

10. The method of claim 9 wherein the average pore size of the porous support material ranges from about 800 to about 1200 angstroms.

11. The method of claim 1 where the steps occur in an HPLC column.

12. The method of claim 9 wherein the pressure of the HPLC column is about 0 psi to 4000 psi.

13. A method of identifying peptide ligands which bind with a specific target protein comprising:

(a) immobilizing randomized peptides on individual chromatographic supports to create a population of supports, each support bead having bound to its surface peptides substantially identical to each other;

(b) contacting the supports of step (a) with a first antibody capable of specifically binding to the target protein, under conditions that allow both specific and nonspecific binding to the target protein, said first antibody also capable of binding specifically and non-specifically to both the supports and peptides on the support;

(c) contacting the supports of step (b) with a second antibody capable of specifically binding to the first antibody and having conjugated thereto an enzyme capable of reacting with at least two different substrates to produce two different color changes, under conditions sufficient to bind the second antibody to the first antibody, said second antibody also capable of binding specifically and non-specifically to both the supports and peptides on the support;

(d) adding a first substrate to the supports of step (c) under conditions sufficient to cause a first color change on individual supports having bound thereto the second antibody;

(e) adding the target protein to the supports of step (d) under conditions sufficient to allow specific binding of the target protein to at least one of the peptides bound to the supports;

(f) contacting the supports of step (e) with the first antibody of step (b) under conditions sufficient to bind that antibody specifically to the target protein;

(g) adding the second antibody of step (c) having the enzyme conjugated thereto to the supports of step (f) under conditions sufficient to bind the second antibody specifically to the first antibody bound to the target protein bound to the peptides bound to the supports;

(h) adding a second substrate to the supports of step (g) under conditions sufficient to cause a second and different color change which distinguishes those supports having bound thereto the peptides which bind with the target protein;

(i) separating the supports having the peptide that binds to the target protein on the basis of the color change caused by the preceding step; and (j) sequencing the peptide on the support separated in step (i).

14. The method of claim 13 wherein there are wash steps between steps (a) and (b), (b) and (c), (c) and (d), (e) and (f), (f) and (g), and (g) and (h).

15. The method of identifying peptides according to claim 13, wherein the support material comprises porous hydrophilic resin beads having an average pore size ranging from about 800 to about 1200 angstroms.

16. The method of identifying peptides of claim 13 wherein the peptides have a length ranging from about 3 to 10 amino acid residues.

17. The method of claim 13 wherein the supports are contained within a column.

18. The method of claim 17 wherein the column is attached to an automated chromatography apparatus.

19. In a method of identifying a ligand molecule that binds to a target molecule, wherein the method comprises:

using the target molecule to probe a random library of ligand molecules immobilized upon a substrate, and then using detection reagents to produce an observable color, said observable color indicating binding between the target molecule and the ligand molecule upon said substrate, the improvement comprising the further step of:

prior to probing the random library with the target molecule, using the detection reagents to probe the same random library of ligand molecules, said probing with the detection reagents causing production of a different observable color than that produced by the interaction of the target molecule and the ligand molecule upon the substrate, said different observable color indicating reaction of the detection reagents with the library of ligand molecules immobilized upon said substrate, the two different observable colors produced by the detection systems serving to distinguish binding between the target molecule and the ligand molecule from reaction of the detection reagents with the library of ligand molecules immobilized upon said substrate.

* * * * *